(12) United States Patent
Nago et al.

(10) Patent No.: US 8,785,710 B2
(45) Date of Patent: Jul. 22, 2014

(54) PARAFFIN PURIFICATION METHOD AND APPARATUS

(75) Inventors: Hiroaki Nago, Hyogo (JP); Shinichi Tai, Hyogo (JP); Junichi Kawakami, Hyogo (JP); Hiroyuki Hata, Hyogo (JP); Shigeru Morimoto, Hyogo (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 135 days.

(21) Appl. No.: 13/139,422

(22) PCT Filed: Dec. 21, 2009

(86) PCT No.: PCT/JP2009/071222
§ 371 (c)(1),
(2), (4) Date: Jun. 13, 2011

(87) PCT Pub. No.: WO2010/074019
PCT Pub. Date: Jul. 1, 2010

(65) Prior Publication Data
US 2011/0245575 A1    Oct. 6, 2011

(30) Foreign Application Priority Data
Dec. 24, 2008 (JP) .................. 2008-327538

(51) Int. Cl.
| | |
|---|---|
| *C07C 7/11* | (2006.01) |
| *C10L 3/10* | (2006.01) |
| *C10G 21/08* | (2006.01) |
| *C10G 70/00* | (2006.01) |
| *C07C 7/00* | (2006.01) |
| *C10G 21/28* | (2006.01) |

(52) U.S. Cl.
CPC . *C10G 21/08* (2013.01); *C07C 7/11* (2013.01); *C10G 2300/1081* (2013.01); *C10L 3/10* (2013.01); *C10G 70/00* (2013.01); *C10G 2300/1088* (2013.01); *C07C 7/005* (2013.01); *C10G 21/28* (2013.01)
USPC .......................... 585/844; 585/834; 585/843

(58) Field of Classification Search
USPC ............ 585/843, 844, 833, 834; 95/187, 240; 96/234
See application file for complete search history.

(56) References Cited

U.S. PATENT DOCUMENTS 2,077,041 A  *  4/1937  Davis et al. ................... 585/809
2,363,309 A  *  11/1944  Friedman et al. ............. 208/279
(Continued)

FOREIGN PATENT DOCUMENTS

| JP | 2001-507682 | 6/2001 |
|---|---|---|
| JP | 2006-508176 | 3/2006 |
| JP | 2006-147866 | 6/2006 |
| WO | WO 98/25871 | 6/1998 |
| WO | WO 00/26326 | 5/2000 |
| WO | WO 2004/50590 | 6/2004 |

OTHER PUBLICATIONS

Padin et al. "New sorbents for olefin/paraffin separations by adsorption via π-complexation: synthesis and effects of substrates". Chemical Engineering Science 55 (2000) 2607-2616.

(Continued)

*Primary Examiner* — In Suk Bullock
*Assistant Examiner* — Candace R Chouinard
(74) *Attorney, Agent, or Firm* — Hamre, Schumann, Mueller & Larson, P.C.

(57) ABSTRACT

A method for purifying a paraffin from a source material containing a paraffin having 2 to 6 carbon atoms and an olefin having 2 to 6 carbon atoms includes a first step of bringing the source material into contact with a silver ion-containing solution (absorption liquid) at a predetermined temperature and pressure in an absorption column 1 and recovering a non-absorbed gas not absorbed by the absorption liquid while the olefin in the source material is preferentially absorbed by the absorption liquid, and a second step of desorbing and discharging a gas component from the absorption liquid having undergone the first step at a predetermined temperature and pressure in a desorption column 2. The first step and the second step are performed continuously in parallel while the absorption liquid is circulated between the first step and the second step.

8 Claims, 2 Drawing Sheets

(56) References Cited

U.S. PATENT DOCUMENTS

| | | | |
|---|---|---|---|
| 2,463,482 | A | 3/1947 | Francis |
| 2,515,140 | A * | 7/1950 | Strand .......................... 585/844 |
| 5,859,304 | A | 1/1999 | Barchas et al. |
| 2008/0223754 | A1 * | 9/2008 | Subramanian et al. ......... 208/86 |

OTHER PUBLICATIONS

Rege et al. "Propane/propylene separation by pressure swing adsorption: sorbent comparison and multiplicity of cyclic steady states". Chemical Engineering Science 57 (2002) 1139-1149.

Padin et al. "Molecular sieve sorbents for kinetic separation of propane/propylene". Chemical Engineering Science 55 (2000) 4525-4535.

Safarik et al. "Olefin/Paraffin Separations by Reactive Absorption", *Ind. Eng. Chem. Res.*, No. 37, pp. 2571-2581 (1998).

Chang et al. "Continuous process for propylene/propane separation by use of silver nitrate carrier and zirconia porous membrane", *Journal of Membrane Science*, vol. 205, pp. 91-102 (2002).

Nymeijer et al. "Super selective membranes in gas-liquid membrane contactors for olefin/paraffin separation", *Journal of Membrane Science*, vol. 232, pp. 107-114 (2004).

Teramoto et al. "Ethylene/ethane separation and concentration by hollow fiber facilitated transport membrane module with permeation of silver nitrate solution", *Separation and Purification Technology*, vol. 44, pp. 19-29 (2005).

* cited by examiner

PARAFFIN PURIFICATION METHOD AND APPARATUS

This application is a national stage entry of PCT/JP2009/07122 filed Dec. 21, 2009 which claims priority to JP 2008-327538 filed Dec. 24, 2008.

TECHNICAL FIELD

The present invention relates to a method and an apparatus for concentrating/purifying a paraffin from a source material composed mainly of a lower paraffin (a paraffin having 2 to 6 carbon atoms) such as propane.

BACKGROUND ART

Propane which is an example of a lower paraffin is used in the field of electronic materials such as semiconductors, and the application requires propane to have a purity as high as possible.

A source gas composed mainly of propane used as a source material for purification contains impurities such as propylene. As methods for purifying a propane gas from the source gas, for example, a method using distillation, a method using membrane separation, a method using adsorptive separation, and the like are known.

The method using distillation requires a large number of theoretical stages for separation because propane and propylene have close boiling points (a difference in boiling point of 4.9° C.). Accordingly, large scale equipment and setting of precise distillation conditions are required, which is a significant barrier to industrial practical application of the method for purifying highly pure propane using distillation.

The method using membrane separation has a low single-pass purification efficiency, and therefore by allowing a source material to pass through a separation membrane a plurality of times for obtaining highly pure propane. However, as the purity of the propane obtained is increased, the recovery rate is reduced to a very low level (see, for example, Patent Document 1).

As adsorptive separation, a method using a silica gel to which silver nitrate has been coated as an adsorbent (see Non-Patent Document 1 below), a method using a silica gel to which silver nitrate has been coated and AlPO-14 as an adsorbent (see Non-Patent Document 2 below), a method using a silica gel to which silver nitrate has been coated and zeolite 4A as an adsorbent (see Non-Patent Document 3 below), and the like are known. However, it is difficult to obtain highly pure propane at a high recovery rate with the methods using adsorbents. This is presumably because, for example, propane is adsorbed on a portion where silver nitrate is not coated, and thus selective adsorption of propylene is not satisfactory.

As described above, a large number of methods have been considered to obtain highly pure propane from a source gas, but there is a trade-off relationship between the recovery rate of propane from a source gas and the purity of propane obtained.

Patent Document 1:
JP 2006-508176 A
Non-Patent Document 1:
New sorbents for olefin/paraffin separations by adsorption via π-complexation: synthesis and effects of substrates, Joel Padin, Ralph T. Yang, Chemical Engineering Science 55 (2000) 2607-2616

Non-Patent Document 2:
Propane/propylene separation by pressure swing adsorption: sorbent comparison and multiplicity of cyclic steady states, Salil U. Rege, Ralph T. Yang, Chemical Engineering Science 57 (2002) 1139-1149
Non-Patent Document 3:
Molecular sieve sorbents for kinetic separation of propane/propylene, Joel Padin, Salil U. Rege, Ralph T. Yang, Linda S. Cheng, Chemical Engineering Science 55 (2000) 4525-4535

DISCLOSURE OF INVENTION

The present invention has been conceived under the above circumstances, and it is an object of the present invention to, when a paraffin is purified from a source material containing a paraffin having 2 to 6 carbon atoms such as propane and an olefin having 2 to 6 carbon atoms such as propylene, increase the purity and recovery rate of the paraffin obtained.

A paraffin purification method provided by a first aspect of the present invention is a method for purifying a paraffin from a source material containing a paraffin having 2 to 6 carbon atoms and an olefin having 2 to 6 carbon atoms, the method including: a first step of bringing the source material into contact with an absorption liquid containing a silver ion at a first temperature and a first pressure and recovering a non-absorbed gas not absorbed by the absorption liquid while the olefin in the source material is preferentially absorbed by the absorption liquid; and a second step of desorbing and discharging a gas component from the absorption liquid having undergone the first step at a second temperature and a second pressure, wherein the first step and the second step are performed continuously in parallel while the absorption liquid in the first step and the absorption liquid in the second step are circulated.

According to conventional findings, olefin having a double bond forms a complex with silver ions, but paraffin does not form a complex with silver ions. It is known that due to this chemical properties, the solubility of olefin in an absorption liquid (for example, an aqueous silver nitrate solution) containing silver ions is much greater than the solubility of paraffin in the absorption liquid under given conditions. The present inventors studied in depth on a method for obtaining a highly pure paraffin at a high recovery rate from a source material containing a lower paraffin (for example, a paraffin having 2 to 6 carbon atoms) and a lower olefin (for example, an olefin having 2 to 6 carbon atoms) by utilizing the difference in solubility between paraffin and olefin in the absorption liquid containing silver ions, and found that paraffin can be obtained at a high purity and a high recovery rate by performing an operation (first step) of causing an absorption liquid to absorb a source gas and an operation (second step) of desorbing and discharging a dissolved gas from the absorption liquid continuously in parallel, based on which the present invention has been accomplished. Because a paraffin having 2 to 6 carbon atoms and an olefin having 2 to 6 carbon atoms have boiling points lower than water, when the paraffin and the olefin are mixed with the absorption liquid, the paraffin and the olefin preferentially boil into the gas phase.

Preferably, the absorption liquid is an aqueous silver nitrate solution.

Preferably, the second pressure is set lower than the first pressure.

Preferably, the second temperature is set higher than the first temperature.

Preferably, the contact between the source material and the absorption liquid in the first step is performed by countercurrent contact.

Examples of the paraffin having 2 to 6 carbon atoms include ethane, propane, cyclopropane, n-butane, isobutane, cyclobutane, methylcyclopropane, n-pentane, isopentane, neopentane, cyclopentane, methylcyclobutane, dimethylcyclopropane, n-hexane, 2-methylpentane, 3-methylpentane, 2,2-dimethylbutane, 2,3-dimethylbutane, cyclohexane, methylcyclopentane, 1,2-dimethylcyclobutane and trimethylcyclopropane.

Examples of the olefin having 2 to 6 carbon atoms include ethylene, propylene, cyclopropene, 1-butene, 2-butene, isobutene, cyclobutene, 1-methylcyclopropene, 2-methylcyclopropene, methylidenecyclopropane, isobutylene, 1,3-butadiene, 1,2-butadiene, cyclopentene, 2-methyl-1-butene, 1-pentene, 2-pentene, 2-methyl-2-butene, 1,4-pentadiene, 1,3-pentadiene, cyclopentene, methylenecyclobutane, vinylcyclopropane, 3-methyl-1,2-butadiene, 1,2-pentadiene, isoprene, 2,3-pentadiene, 1-hexene, 2-hexene, 3-hexene, 3,3-dimethyl-1-butene, 2,3-dimethyl-1-butene, 2,3-dimethyl-2-butene, 2-methyl-1-pentene, 3-methyl-1-pentene, 4-methyl-1-pentene, 2-methyl-2-pentene, 3-methyl-2-pentene, 4-methyl-2-pentene, 2-ethyl-1-butene, 1,5-hexadiene, 1,4-hexadiene, 2,4-hexadiene, 2-methyl-1,3-pentadiene, 2-methyl-1,4-pentadiene, 3-methyl-1,3-pentadiene, 4-methyl-1,3-pentadiene, 2,3-dimethyl-1,3-butadiene, cyclohexene, 1,3-hexadiene, 2,4-hexadiene, 1-methyl-1-cyclopentene, 3-methyl-1,3-pentadiene, 3-methyl-1,4-pentadiene and methylenecyclopentane.

A paraffin purification apparatus provided by a second aspect of the present invention is a paraffin purification apparatus for purifying a paraffin from a source material containing a paraffin having 2 to 6 carbon atoms and an olefin having 2 to 6 carbon atoms, the apparatus including: an absorption column for bringing the source material into contact with an absorption liquid containing a silver ion at a first temperature and a first pressure and recovering a non-absorbed gas not absorbed by the absorption liquid while the olefin in the source material is preferentially absorbed by the absorption liquid; a desorption column for desorbing and discharging the olefin from the absorption liquid having absorbed the olefin at a second temperature and a second pressure; and a circulation means for causing the absorption liquid in the absorption column and the absorption liquid in the desorption column to circulate between the absorption column and the desorption column. With the purification apparatus having such a configuration, the paraffin purification method according to the first aspect of the present invention can be appropriately performed.

According to a preferred embodiment of the present invention, the absorption column includes a column body that holds a part of the absorption liquid, a gas introducing tube that supplies the source material to the absorption liquid at a lower portion of the column body, an absorption liquid drawing tube for withdrawing the absorption liquid having absorbed the olefin from the lower portion of the column body, and a gas drawing tube for withdrawing the paraffin not absorbed by the absorption liquid from an upper portion of the column body, and the absorption liquid circulated from the desorption column is returned to the column body via the gas drawing tube.

According to another preferred embodiment of the present invention, the absorption column includes a column body that holds a part of the absorption liquid, a packed portion packed in the column body above the absorption liquid held in the column body, a gas introducing tube that supplies the source material between the absorption liquid held in the column body and the packed portion column, an absorption liquid drawing tube for withdrawing the absorption liquid having absorbed the olefin from a lower portion of the column body, and a gas drawing tube for withdrawing the paraffin not absorbed by the absorption liquid in the packed portion, and the absorption liquid circulated from the desorption column is returned to the column body such that absorption liquid passes downward through the packed portion.

Other features and advantages of the present invention will become apparent in the following detailed descriptions with reference to the accompanying drawings.

MODES FOR CARRYING OUT THE INVENTION

Hereinafter, as a preferred embodiment of the present invention, a method for concentrating/purifying a paraffin from a source material containing a paraffin having 2 to 6 carbon atoms and an olefin having 2 to 6 carbon atoms will be described specifically with reference to the drawings.

Figure 1:
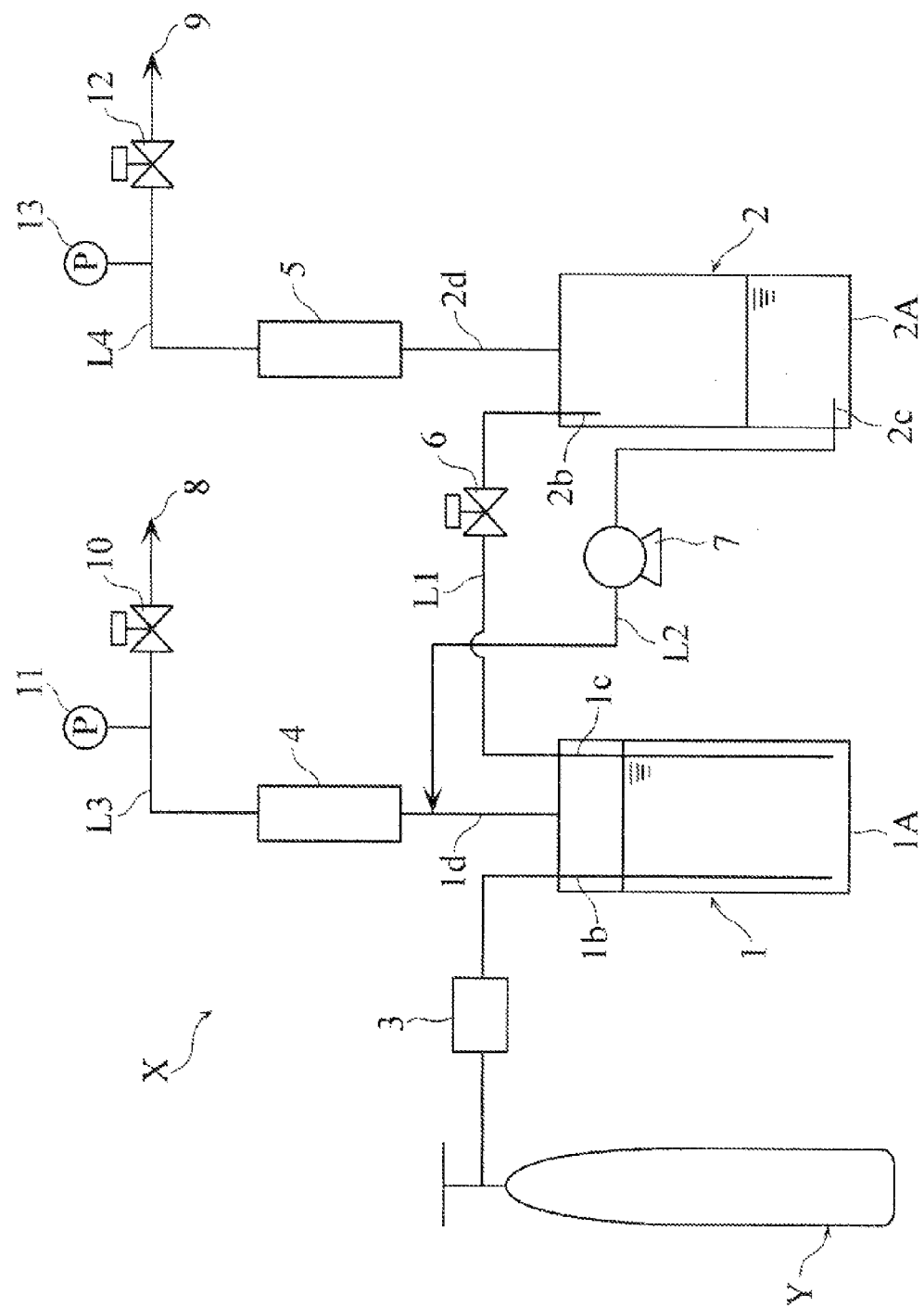
FIG. 1 is a diagram showing an overall configuration of a paraffin purification apparatus according to the present invention.

FIG. 1 is a diagram showing an overall configuration of a paraffin purification apparatus X according to a preferred embodiment of the present invention. The paraffin purification apparatus X is configured to purify a crude paraffin supplied from a gas cylinder Y to obtain a higher-purity paraffin of enhanced purity. The paraffin purification apparatus X includes an absorption column 1, a desorption column 2, a flow controller 3, mist eliminators 4 and 5, a flow control valve 6, a pump 7, a gas recovery port 8, a gas discharge port 9, and pipings for connection of these components.

In the gas cylinder Y, a crude paraffin is stored under high pressure in order to supply the crude paraffin as a source gas to the paraffin purification apparatus X. In the case where the paraffin to be purified is propane, the source gas (crude paraffin) stored in the gas cylinder Y contains, for example, propane as a main component and propylene as an impurity. The following description illustrates an example in which the paraffin to be purified is propane.

The absorption column 1 is provided to bring the source gas into contact with an absorption liquid, and includes a column body 1A, a gas introducing tube 1b, an absorption liquid drawing tube 1c, and a gas drawing tube 1d. The column body 1A is a sealed container which holds therein an absorption liquid made up of a silver ion-containing solution. The absorption liquid can be, for example, an aqueous silver nitrate solution prepared to have a predetermined concentration. The gas introducing tube 1b is provided to introduce the source gas supplied from the gas cylinder Y into the column body 1A, and has an open end in the absorption liquid at a lower portion of the column body 1A. The open end of the gas introducing tube 1b may, for example, be provided as a simple extension of the tube or as a diffuser tube portion. The absorption liquid drawing tube 1c is provided to draw the absorption liquid in the column body 1A to the outside of the column, and has an open end in the absorption liquid at the lower portion of the column body 1A. The gas drawing tube 1d is provided to draw a gas (non-absorbed gas) not absorbed by the absorption liquid to the outside of the column, and is connected to an upper portion of the column body 1A.

As the absorption column 1 having such a configuration, for example, use may be made of a known bubble column, packed column, wetted-wall column, spray column, scrubber, stepwise shelf column or the like. The absorption column 1 also includes a temperature regulation mechanism (not shown) for maintaining the absorption liquid in the column body 1A at a desired temperature. The temperature regulation mechanism includes, for example, a jacket that causes a gaseous or liquid temperature regulating medium to flow around the column body 1A.

The desorption column 2 is provided to desorb the gas component absorbed by the absorption liquid in the absorption column 1, and includes a column body 2A, an absorption liquid introducing tube 2b, an absorption liquid drawing tube 2c, and a gas drawing tube 2d. The column body 2A is a sealed container, and is capable of holding a predetermined amount of absorption liquid therein. The absorption liquid introducing tube 2b is provided to introduce the absorption liquid drawn from the absorption column 1 into the column body 2A, and has an open end in an upper space of the column body 2A. The absorption liquid introducing tube 2b is connected to the absorption liquid drawing tube 1c of the absorption column 1 via a piping L1 and the flow control valve 6.

The absorption liquid drawing tube 2c is provided to draw the absorption liquid in the desorption column 2 to the outside of the column, and has an open end in a lower portion of the absorption liquid. The absorption liquid drawing tube 2c is connected to an intermediate portion of the gas drawing tube 1d of the absorption column 1 via a piping L2 and the pump 7. The pump 7 pumps the absorption liquid in the desorption column 2 to the gas drawing tube 1d. The absorption liquid drawing tube 1c, the piping L1, the flow control valve 6, the absorption liquid introducing tube 2b, the absorption liquid drawing tube 2c, the piping L2, the pump 7 and the gas drawing tube 1d constitute a circulation means for circulation of the absorption liquid between the absorption column 1 and the desorption column 2. The gas drawing tube 2d is provided to draw the gas desorbed from the absorption liquid to the outside of the desorption column 2, and is connected to the upper portion of the column body 2A.

The desorption column 2 having such a configuration is preferably capable of dispersing the absorption liquid, and use may be made of a known packed column, spray column or the like. The desorption column 2 also includes a temperature regulation mechanism (not shown) for maintaining the absorption liquid in the column body 2A at a desired temperature. The temperature regulation mechanism includes, for example, a jacket that causes a gaseous or liquid temperature regulating medium to flow around the column body 1A.

The flow controller 3 controls the flow rate of the source gas supplied from the gas cylinder Y to a predetermined flow rate.

The mist eliminator 4 is connected to the gas drawing tube 1d of the absorption column 1, and separates mist contained in the non-absorbed gas that has been drawn via the gas drawing tube 1d. The mist eliminator 4 is connected to a piping L3 for guiding the gas that has passed through the mist eliminator 4 to the gas recovery port 8. The piping L3 is provided with a back pressure valve 10 and a pressure gauge 11. The degree of opening of the back pressure valve 10 is regulated such that the inside of the absorption column 1 has a predetermined pressure.

The mist eliminator 5 is connected to the gas drawing tube 2d of the desorption column 2, and is provided to separate mist contained in the desorbed gas that has been drawn via the gas drawing tube 2d. The mist eliminator 5 is connected to a piping L4 for guiding the gas that has passed through the mist eliminator 5 to the gas discharge port 9. The piping L9 is provided with a back pressure valve 12 and a pressure gauge 13. The degree of opening of the back pressure valve 12 is regulated such that the inside of the desorption column 2 has a predetermined pressure.

When the paraffin purification method of the present invention is carried out using the paraffin purification apparatus X having the above configuration, a source gas is continuously supplied from the gas cylinder Y into the column body 1A of the absorption column 1 via the flow controller 3 and the gas introducing tube 1b.

As described above, in the case where the paraffin to be purified is propane, the source gas contains propane as a main component and propylene as an impurity. The propane concentration and the propylene concentration in the source gas supplied from the gas cylinder Y can be, for example, 98 to 99.5% and 0.5 to 2.0%, respectively, in molar ratio. The amount of source gas supplied to the absorption column 1 can be, for example, 1 dm$^3$/s to 100 dm$^3$/s per square meter of the cross-sectional area of the column, and in laboratory scale, the amount can be, for example, approximately 40 to 4000 cm$^3$/min.

In the column body 1A of the absorption column 1, when the source gas is emitted from the end of the gas introducing tube 1b, the source gas comes into contact with the absorption liquid and thereby is gradually absorbed by the absorption liquid. Because the solubility of olefin (propylene) in the absorption liquid (for example, an aqueous silver nitrate solution) is significantly greater than the solubility of paraffin (propane), the olefin (propylene) in the source gas is preferentially absorbed by the absorption liquid. For this reason, as the source gas rises upward in the absorption liquid while being absorbed, the olefin concentration (propylene concentration) in the gas decreases, whereas the paraffin concentration (propane concentration) increases.

On the other hand, as for the absorption liquid in the column body 1A, the absorption liquid that has absorbed the source gas in the absorption column 1 flows from the lower portion of the column body 1A to the outside of the absorption column 1 via the absorption liquid drawing tube 1c at a predetermined flow rate, and the absorption liquid from which the gas component has been desorbed in the desorption column 2, which will be described later, flows into the column through the upper portion of the column body 1A via the pump 7 and the gas drawing tube 1d. Accordingly, in the absorption liquid (liquid bath) in the column body 1A, a descending flow occurs. The source gas emitted from the gas introducing tube 1b is thereby brought into counter-current contact with the absorption liquid, and the non-absorbed gas that was not absorbed flows up to the upper portion space in the column body 1A. The non-absorbed gas is sent to the mist eliminator 4 via the gas drawing tube 1d, the liquid component is separated and removed from the non-absorbed gas, and the resulting gas is sent to the outside of the system via the piping L3 and the gas recovery port 8 for recovery. The liquid component separated by the mist eliminator 4 drops back into the absorption column 1 via the gas drawing tube 1d, in the form of droplets.

It is preferable that the absorption liquid (for example, an aqueous silver nitrate solution) in the absorption column 1 has a high silver nitrate concentration because when the silver nitrate concentration is high, the amount of olefin absorbed per unit volume/unit time increases. In the case of the olefin being propylene, from the viewpoint of practical application, the concentration of the aqueous silver nitrate solution can be, for example, in a range of 1 to 6 mol/dm$^3$, and more preferably 3 to 5 mol/dm$^3$. As for the temperature of the aqueous silver nitrate solution, a lower temperature is advantageous because the amount of propylene absorbed increases. The temperature of the aqueous silver nitrate solution can be, for example, in a range of 0 to 60° C., and more preferably 0 to 40° C. The internal pressure of the column body 1A is preferably high in a specified range because the amount of propylene absorbed increases. From the viewpoint of practical application, the internal pressure of the column body 1A can be, for example, 0.1 to 0.8 MPa (gauge pressure).

In this manner, in the absorption column 1, the continuously supplied source gas makes contact with the absorption liquid and thereby the olefin (propylene) in the source gas is preferentially absorbed by the absorption liquid, whereas the non-absorbed gas is recovered outside the column. The non-absorbed gas is recovered from the absorption liquid that has preferentially absorbed the olefin (propylene) in the source gas, and therefore has a higher paraffin (propane) concentration than the source gas.

The absorption liquid that has absorbed the source gas in the absorption column 1 flows into the column body 2A of the desorption column 2 via the absorption liquid drawing tube 1c, the piping L1, the flow control valve 6 and the absorption liquid introducing tube 2b due to a difference between the internal pressure of the absorption column 1 and that of the desorption column 2. If the pressure difference is small, a pump may be used to transfer the absorption liquid. The amount of absorption liquid flowing into the column body 2A is adjusted by the flow control valve 6, and can be, for example, 0.1 to 10 dm$^3$/s per square meter of the cross section of the column. In the laboratory scale, the amount can be, for example, approximately 5 to 500 cm$^3$/min.

In the column body 2A, the gas component that has been absorbed by the absorption liquid is desorbed. From the viewpoint of efficiently desorbing the gas component, the internal temperature of the column body 2A is preferably set higher than that of the absorption column 1, and the internal pressure is preferably set lower than that of the absorption column 1. The temperature of the absorption liquid in the column body 2A can be, for example, 10 to 70° C., and more preferably 20 to 70° C. The internal pressure of the column body 2A can be, for example, in the case of the olefin being propylene, −0.09 to 0.3 MPa (gauge pressure), and more preferably 0 to 0.3 MPa (gauge pressure). The desorbed gas (mainly, propylene) desorbed from the absorption liquid is sent to the mist eliminator 5 via the gas drawing tube 2d, the liquid component is removed, and the resulting gas is discharged via the piping L4 and the gas discharge port 9. The liquid component separated by the mist eliminator 5 drops back into the desorption column 2 via the gas drawing tube 2d, in the form of droplets.

The absorption liquid from which the gas component has been desorbed is pumped to the gas drawing tube 1d via the absorption liquid drawing tube 2c by the pump 7, and thereafter drops into the column body 1A of the absorption column 1. The flow rate of the absorption liquid pumped by the pump 7 at this time is set at the same level as the flow rate of the absorption liquid flowing from the absorption column 1 to the desorption column 2 via the flow control valve 6. The absorption liquid in the absorption column 1 and the absorption liquid in the desorption column 2 thereby circulate at a predetermined flow rate between the absorption column 1 and the desorption column 2 (circulation step).

In the manner described above, in the desorption column 2, the gas component in the absorption liquid continuously flowing at a predetermined flow rate is desorbed and the desorbed gas (mainly, propylene) is discharged to the outside of the column.

A highly pure paraffin (propane) can be obtained by purifying a source gas such as a crude paraffin (propane) containing an olefin (propylene) as an impurity in the above-described manner.

The solubility of propylene in an aqueous silver nitrate solution is described in detail in Solubility of Propylene in Aqueous Silver Nitrate, I. H. Cho, D. L. Cho, H. K. Yasuda, and T. R. Marrero, J. Chem. Eng. Data 1995, 40, 102-106. This document also states that the solubility of propane in an aqueous silver nitrate solution is small.

The present inventors examined the effects of the method for purifying propane from a crude propane containing propylene as an impurity by a batch method, using the gas/liquid phase equilibrium of propane and propylene in an aqueous silver nitrate solution described in the above document. Specifically, a crude propane was introduced into a container charged with an aqueous silver nitrate solution to cause the aqueous silver nitrate solution to absorb propylene, and thereafter the gas phase component (non-absorbed gas component) in the container was analyzed. As a result, it was found that propylene was also contained in the gas phase although the amount was very small. It was also found that, in order to obtain a highly pure propane (for example, with a purity of 99.99% or more), it is necessary to reduce the amount of crude propane introduced into the aqueous silver nitrate solution, and therefore this method is not industrially useful. Under these circumstances, the present inventors studied in depth and developed an industrially useful method for obtaining a highly pure propane while maintaining a high propane recovery rate, consequently arriving at the present invention.

The reason that the present invention can increase the recovery rate of highly pure paraffin by efficiently purifying a paraffin from a crude paraffin containing an olefin is not clearly known, but the following reason can be considered, for example. According to the present embodiment, a crude paraffin (source gas) containing an olefin is introduced from the lower portion of the column body 1A of the absorption column 1, and flows upward while the olefin is preferentially absorbed by the aqueous silver nitrate solution. Accordingly, the olefin concentration near the gas/liquid interface in the upper portion of the aqueous silver nitrate solution in the column body 1A is presumed to be lower than that in the lower portion of the column body 1A. Because the aqueous silver nitrate solution having a relatively high olefin concentration in the lower portion of the column body 1A is continuously sent to the column body 2A of the desorption column 2, where the olefin is desorbed, and thereafter the aqueous silver nitrate solution having a low olefin concentration flows back from the upper portion of the column body 1A of the absorption column 1, it is presumed that the difference in olefin concentration between the lower portion and the upper portion of the aqueous silver nitrate solution in the column body 1A is maintained. On the other hand, it is presumed that the olefin concentration of the gas phase of the column body 1A of the absorption column 1 depends on the olefin concentration near the gas/liquid interface of the aqueous silver nitrate solution, and thus a highly pure paraffin can be efficiently obtained as compared to the case where the olefin concentration in the aqueous silver nitrate solution is uniform, as in the batch method.

In the case of the continuous method as in the present embodiment in which the impurity (olefin) in the source gas is absorbed by and desorbed from the absorption liquid (for example, an aqueous silver nitrate solution) continuously in parallel, by adjusting various conditions such as the internal temperature and pressure of the column, the supply form of the source gas, and the conditions of the absorption liquid (concentration, amount of usage and circulating flow rate), it is possible to obtain a highly pure paraffin at a high recovery rate.

According to the present invention, by adjusting the various conditions according to the purpose, it is possible to obtain a highly pure paraffin at a high recovery rate using various crude paraffins of different concentrations as the source material. For example, when a crude paraffin having a purity of 99.5% is used as the source material, a highly pure paraffin having a purity of 99.95% or more can be obtained at a recovery rate of 95% or more. Also, when a crude paraffin having a purity of 90% is used as the source material, for example, a highly pure paraffin having a purity of 99% or more can be obtained at a recovery rate 90% or more. Also, when a crude paraffin having a purity of 50% is used as the source material, for example, a paraffin having an increased purity of 95% or more can be obtained at a recovery rate of 80% or more.

An embodiment of the present invention has been described above, but the scope of the present invention is not limited to the embodiment described above. The specific configuration of the paraffin purification apparatus of the present invention and the paraffin purification method of the present invention can be changed in many ways without departing from the concept of the present invention.

For example, in the method of bringing the source gas and the absorption liquid into contact in the absorption column 1, they do not necessarily need to come into counter-current contact, and the absorption liquid drawing tube 1c may be provided such that its end is open in the upper portion of the liquid bath of the absorption liquid. In this case, the region where the absorption liquid and the source gas come into counter-current contact is limited to a small region above the end of the absorption liquid drawing tube 1c, but even with this embodiment, a highly pure paraffin can be obtained at a high recovery rate.

Figure 2:
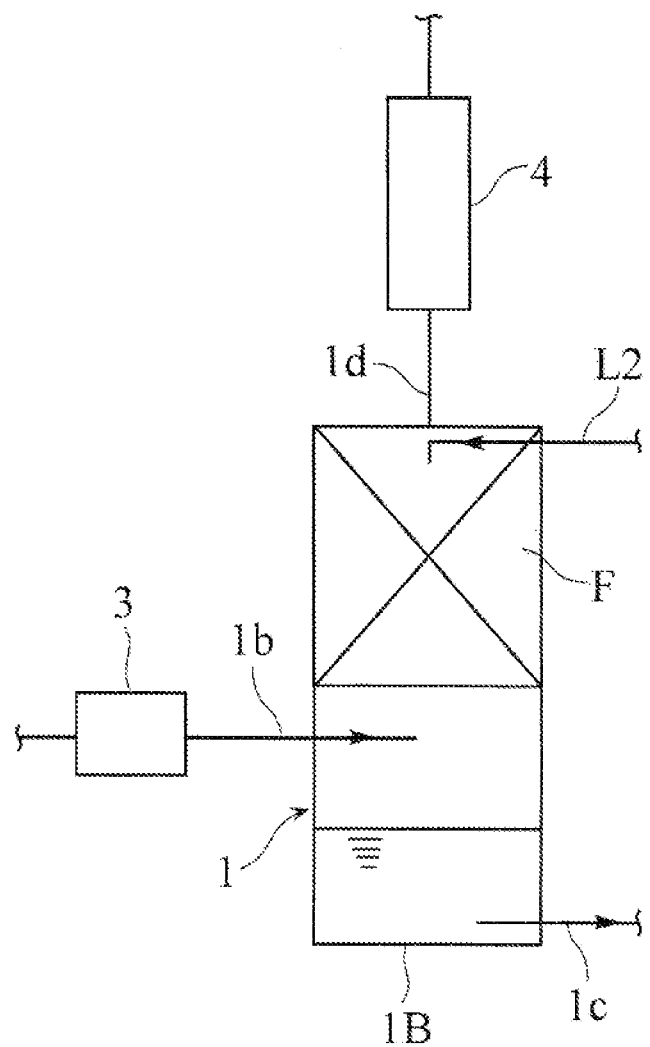
FIG. 2 is a diagram showing an overall configuration of an absorption column according to the present invention.

Also, in the absorption column 1 of the paraffin purification apparatus X shown in FIG. 1, a column body 1B (packed column) shown in FIG. 2 may be used instead of the column body 1A (bubble column). In the column body 1B, a packing material F is packed in an upper portion of the column, and the piping L2 for introducing the absorption liquid pumped from the desorption column 2 into the column is open at an upper portion of the packing material F. The end of the gas introducing tube 1b is open in an intermediate space of the column. When a source gas is emitted from the end of the gas introducing tube 1b into the column body 1B, the source gas efficiently comes into counter-current contact with the absorption liquid introduced via the piping L2 at the surface of the packing material F, and is gradually absorbed by the absorption liquid.

The embodiment described above is an example in which the paraffin is propane, but the "paraffin" as used in the present invention can be a paraffin having 2 to 6 carbon atoms. The paraffin contains an olefin having a similar boiling point as an impurity. The paraffin and olefin having similar boiling points can be, for example, those having the same number of carbon atoms. An olefin having a double bond forms a complex with silver ions, as with propylene, and therefore the same effects as those described above in connection with propylene can be obtained.

A paraffin and olefin having 5 or 6 carbon atoms have a boiling point higher than a paraffin and olefin having 2 to 4 carbon atoms (for example, C6: n-hexane and 1-hexene with 68.7° C. and 63.5° C., respectively, and C5: n-pentane and 1-pentene with 36.0° C. and 30.1° C., respectively), and are liquid at room temperature. In this case, the source material may be introduced into the column body 1A of the absorption column 1 in the form of a liquid, or may be heated into a gas before introduction. By maintaining the internal temperature of the column body 1A at a temperature that is greater than or equal to the boiling point of a target paraffin and at which a target olefin can be preferentially absorbed by the absorption liquid, the paraffin is vaporized in the absorption column 1A for discharging, and the olefin is preferentially absorbed by the absorption liquid. The internal temperature and pressure of the column body 2A of the desorption column 2 is set to a level at which the olefin that has been absorbed by the absorption liquid can be desorbed. For example, in the case where the column body 1A and the column body 2A have the same internal pressure, the internal temperature of the column body 2A is set higher than that of the column body 1A.

As an example, in the case where the source material contains n-hexane and 1-hexene, the internal temperature of the column body 1A is required to be greater than or equal to the boiling point of n-hexane (68.7° C.), and can be, for example, 75° C. Most of n-hexane is not absorbed and thus emitted from the absorption column 1 in the form of a gas as a non-absorbed gas, and can be recovered as highly pure n-hexane. Most of 1-hexene is absorbed by the absorption liquid because it is in the form of a silver complex although the internal temperature of the column body 1A is greater than or equal to the boiling point, and the absorption liquid in which 1-hexene has been dissolved is sent to the desorption column 2. The internal temperature of the column body 2A of the desorption column 2 is set higher (for example, 85° C.) than that of the column body 1A of the absorption column 1, and thereby 1-hexene is emitted and discharged in the form of a gas.

EXAMPLES

The usability of the present invention will be described next by way of examples.

Example 1

In this example, the paraffin purification apparatus X shown in FIG. 1 was used to purify propane from a crude propane gas as the source gas.

In this example, cylindrical tubes made of stainless steel (54.9 mm in inner diameter and 500 mm in height, with a volume of 1185 cm$^3$) were used as the column body 1A of the absorption column 1 (bubble column) and the column body 2A of the desorption column 2. As the absorption liquid, a 3 mol/dm$^3$ aqueous silver nitrate solution was held in the column body 1A of the absorption column 1, in an amount of 735 cm$^3$ (depth: 310 mm), and an aqueous silver nitrate solution of the same concentration was held in the column body 2A of the desorption column 2, in an amount of 355 cm$^3$ (depth: 150 mm). As the conditions in the absorption column 1, the internal pressure of the column body 1A was adjusted to 0.6 MPa (gauge pressure) and the internal temperature was adjusted to 15° C. As the conditions in the desorption column 2, the internal pressure of the column body 2A was adjusted to 0 MPa (gauge pressure) and the internal temperature was adjusted to 50° C. The aqueous silver nitrate solutions held in the column bodies 1A and 2A were circulated between the column bodies 1A and 2A at a flow rate of 19 cm$^3$/min. As the source gas supplied to the absorption column 1A, a source gas having a propane concentration of 99.5% and a propylene concentration of 0.5% was used. The source gas was supplied at a flow rate of 300 cm$^3$/min.

The result of analysis of the purified gas from the absorption column 1 during steady-state operation is shown in Table 1. In this example, a highly pure propane gas (propylene concentration of 350 ppm) having a purity of 99.96% was obtained as the purified gas from the absorption column 1 in an amount of 298.60 cm$^3$/min and at a recovery rate of 99.53%. Also, propylene was discharged from the desorption column 2 in an amount of 1.40 cm$^3$/min with a discarded rate of 0.47%.

Example 2

In this example, in the absorption column 1 of the paraffin purification apparatus X shown in FIG. 1, the column body 1B (packed column) shown in FIG. 2 was used instead of the column body 1A (bubble column).

In this example, a cylindrical tube made of stainless steel (28.4 mm in inner diameter and 1000 mm in height, with a volume of 633 cm$^3$) was used as the column body 1B of the absorption column 1. As the packing material F, ¼ inch interlox saddle was packed in the column, in an amount of 507 cm$^3$ (800 mm high). A 3 mol/dm$^3$ aqueous silver nitrate solution was held in the column body 1B of the absorption column 1, in an amount of 317 cm$^3$ (depth: 500 mm), and an aqueous silver nitrate solution of the same concentration was held in the column body 2A of the desorption column 2, in an amount of 127 cm$^3$ (depth: 200 mm). As the conditions in the absorption column 1, the internal pressure of the column body 1B was adjusted to 0.6 MPa (gauge pressure) and the internal temperature was adjusted to 15° C. As the conditions in the desorption column 2, the internal pressure of the column body 2A was adjusted to 0 MPa (gauge pressure) and the internal temperature was adjusted to 50° C. The aqueous silver nitrate solutions held in the column bodies 1B and 2A were circulated between the column bodies 1B and 2A at a flow rate of 19 cm$^3$/min. As the source gas supplied to the absorption column 1B, a source gas having a propane concentration of 99.5% and a propylene concentration of 0.5% was used. The source gas was supplied at a flow rate of 300 cm$^3$/min.

The result of analysis of the purified gas from the absorption column 1 during steady-state operation is shown in Table 1. In this example, a highly pure propane gas (propylene concentration of 320 ppm) having a purity of 99.96% was obtained as the purified gas from the absorption column 1 in an amount of 298.60 cm$^3$/min and at a recovery rate of 99.53%. Also, propylene was discharged from the desorption column 2 in an amount of 1.40 cm$^3$/min with a discarded rate of 0.47%.

Example 3

In this example, the same propane purification apparatus as that used in Example 2 was used, and propane was purified from a source gas under conditions different from those used in Example 2.

In this example, a 3 mol/dm$^3$ aqueous silver nitrate solution was held in the column body 1B of the absorption column 1, in an amount of 317 cm$^3$ (depth: 500 mm), and an aqueous silver nitrate solution of the same concentration was held in the column body 2A of the desorption column 2, in an amount of 127 cm$^3$ (depth: 200 mm). As the conditions in the absorption column 1, the internal pressure of the column body 1B was adjusted to 0.6 MPa (gauge pressure) and the internal temperature was adjusted to 25° C. As the conditions in the desorption column 2, the internal pressure of the column body 2A was adjusted to 0 MPa (gauge pressure) and the internal temperature was adjusted to 50° C. The aqueous silver nitrate solutions held in the column bodies 1B and 2A were circulated between the column bodies 1B and 2A at a flow rate of 19 cm$^3$/min. As the source gas supplied to the absorption column 1B, a source gas having a propane concentration of 99.5% and a propylene concentration of 0.5% was used. The source gas was supplied at a flow rate of 300 cm$^3$/min.

The result of analysis of the purified gas from the absorption column 1 during steady-state operation is shown in Table 1. In this example, a highly pure propane gas (propylene concentration of 500 ppm) having a purity of 99.95% was obtained as the purified gas from the absorption column 1 in an amount of 298.65 cm$^3$/min and at a recovery rate of 99.55%. Also, propylene was discharged from the desorption column 2 in an amount of 1.35 cm$^3$/min with a discarded rate of 0.45%.

Example 4

In this example, the same propane purification apparatus as that used in Examples 2 and 3 was used, and propane was purified from a source gas under conditions different from those used in Examples 2 and 3.

In this example, a 5 mol/dm$^3$ aqueous silver nitrate solution was held in the column body 1B of the absorption column 1, in an amount of 317 cm$^3$ (depth: 500 mm), and an aqueous silver nitrate solution of the same concentration was held in the column body 2A of the desorption column 2, in an amount of 127 cm$^3$ (depth: 200 mm). As the conditions in the absorption column 1, the internal pressure of the column body 1B was adjusted to 0.6 MPa (gauge pressure) and the internal temperature was adjusted to 15° C. As the conditions in the desorption column 2, the internal pressure of the column body 2A was adjusted to 0 MPa (gauge pressure) and the internal temperature was adjusted to 50° C. The aqueous silver nitrate solutions held in the column bodies 1B and 2A were circulated between the column bodies 1B and 2A at a flow rate of 19 cm$^3$/min. As the source gas supplied to the absorption column 1B, a source gas having a propane concentration of 99.5% and a propylene concentration of 0.5% was used. The source gas was supplied at a flow rate of 300 cm$^3$/min.

The result of analysis of the purified gas from the absorption column 1 during steady-state operation is shown in Table 1. In this example, a highly pure propane gas (propylene concentration of 200 ppm) having a purity of 99.98% was obtained as the purified gas from the absorption column 1 in an amount of 298.56 cm$^3$/min and at a recovery rate of 99.52%. Also, propylene was discharged from the desorption column 2 in an amount of 1.44 cm$^3$/min with a discarded rate of 0.48%.

TABLE 1

| | Silver nitrate concentration [mol/dm³] | Absorption conditions | | Desorption conditions | | Purified gas | | |
|---|---|---|---|---|---|---|---|---|
| | | Pressure [MPaG] | Temp. [°C.] | Pressure [MPaG] | Temp. [°C.] | Recovery Rate [%] | Propane Purity [%] | Propylene Concentration [ppm] |
| Ex. 1 | 3 | 0.6 | 15 | 0 | 50 | 99.53 | 99.96 | 350 |
| Ex. 2 | 3 | 0.6 | 15 | 0 | 50 | 99.53 | 99.96 | 320 |
| Ex. 3 | 3 | 0.6 | 25 | 0 | 50 | 99.55 | 99.95 | 500 |
| Ex. 4 | 5 | 0.6 | 15 | 0 | 50 | 99.52 | 99.98 | 200 |

Example 5

In this example, the same purification apparatus as that used in Examples 2 to 4 was used, and purification was performed using crude n-hexane as the source material.

In this example, as the absorption liquid, a 5 mol/dm³ aqueous silver nitrate solution was held in the column body 1B of the absorption column 1, in an amount of 317 cm³ (depth: 500 mm), and an aqueous silver nitrate solution of the same concentration was held in the column body 2A of the desorption column 2, in an amount of 127 cm³ (depth: 200 mm). As the conditions in the absorption column 1, the internal pressure of the column body 1B was adjusted to 0.0 MPa (gauge pressure) and the internal temperature was adjusted to 75° C. As the conditions in the desorption column 2, the internal pressure of the column body 2A was adjusted to 0.0 MPa (gauge pressure) and the internal temperature was adjusted to 85° C. The aqueous silver nitrate solutions held in the column bodies 1B and 2A were circulated between the column bodies 1B and 2A at a flow rate of 19 cm³/min. As the source gas supplied to the absorption column 1, the source material that had been heated and vaporized to have an n-hexane concentration of 99.5% and a 1-hexene concentration of 0.5% was used. The source gas was supplied at a flow rate of 200 cm³/min (75° C.).

The result of analysis of the purified gas from the absorption column 1 during steady-state operation is shown in Table 2. In this example, a highly pure n-hexane gas (1-hexene concentration of 500 ppm) having a purity of 99.95% was obtained as the purified gas from the desorption column 2 in an amount of 198 cm³/min (75° C.) and at a recovery rate of 99.00%. Also, a 1-hexene gas was discharged from the desorption column 2 in an amount of 2.06 cm³/min (85° C.) with a discarded rate of 1.00%.

TABLE 2

| | Silver nitrate concentration [mol/dm³] | Absorption conditions | | Desorption conditions | | Purified gas | | |
|---|---|---|---|---|---|---|---|---|
| | | Pressure [MPaG] | Temp. [°C.] | Pressure [MPaG] | Temp. [°C.] | Recovery rate [%] | n-hexane purity [%] | 1-hexene Concentration [ppm] |
| Ex. 5 | 5 | 0 | 75 | 0 | 85 | 99.00 | 99.95 | 500 |

The invention claimed is:

1. A paraffin purification method for purifying a paraffin from a source material, comprising:
    introducing a source material comprising no less than 90 mol % of a paraffin having 2 to 6 carbon atoms as a main component and an olefin having 2 to 6 carbon atoms as an impurity at a bottom portion of an absorption column;
    contacting the source material with an absorption liquid containing a silver ion at a first temperature and a first pressure, wherein the olefin is absorbed by the absorption liquid to produce a used absorption liquid;
    recovering the paraffin that is not absorbed by the absorption liquid via a gas drawing tube connected to a top of the absorption column;
    introducing the used absorption liquid to a desorption column for desorbing and discharging the olefin at a second temperature and a second pressure to produce a regenerated absorption liquid; and
    returning the regenerated absorption liquid to the absorption column through a return piping that is connected to the desorption column and to the gas drawing tube,
    wherein the absorption and the desorption of the olefin are performed continuously in parallel while the used and regenerated absorption liquids are circulated between the absorption column and the desorption column; and
    wherein the absorption liquid contains no absorption-assisting component other than the silver ion.

2. The paraffin purification method according to claim 1, wherein the absorption liquid is an aqueous silver nitrate solution.

3. The paraffin purification method according to claim 1, wherein the second pressure is set lower than the first pressure.

4. The paraffin purification method according to claim 1, wherein the second temperature is set higher than the first temperature.

5. The paraffin purification method according to claim 1, wherein the source material and the absorption liquid are contacted counter-currently.

6. The paraffin purification method according to claim 1, wherein the paraffin is at least one selected from the group consisting of ethane, propane, cyclopropane, n-butane, isobutane, cyclobutane, methylcyclopropane, n-pentane, isopentane, neopentane, cyclopentane, methylcyclobutane, dimethylcyclopropane, n-hexane, 2-methylpentane, 3-methylpentane, 2,2-dimethylbutane, 2,3-dimethylbutane, cyclohexane, methylcyclopentane, 1,2-dimethylcyclobutane and trimethylcyclopropane.

7. The paraffin purification method according to claim 1, wherein the olefin is at least one selected from the group consisting of ethylene, propylene, cyclopropene, 1-butene, 2-butene, isobutene, cyclobutene, 1-methylcyclopropene, 2-methylcyclopropene, methylidenecyclopropane, isobutylene, 1,3-butadiene, 1,2-butadiene, cyclopentene, 2-methyl-1-butene, 1-pentene, 2-pentene, 2-methyl-2-butene, 1,4-pentadiene, 1,3-pentadiene, cyclopentene, methylenecyclobutane, vinylcyclopropane, 3-methyl-1,2-butadiene, 1,2-pentadiene, isoprene, 2,3-pentadiene, 1-hexene, 2-hexene, 3-hexene, 3,3-dimethyl-1-butene, 2,3-dimethyl-1-butene, 2,3-dimethyl-2-butene, 2-methyl-1-pentene, 3-methyl-1-pentene, 4-methyl-1-pentene, 2-methyl-2-pentene, 3-methyl-2-pentene, 4-methyl-2-pentene, 2-ethyl-1-butene, 1,5-hexadiene, 1,4-hexadiene, 2,4-hexadiene, 2-methyl-1,3-pentadiene, 2-methyl-1,4-pentadiene, 3-methyl-1,3-pentadiene, 4-methyl-1,3-pentadiene, 2,3-dimethyl-1,3-butadiene, cyclohexene, 1,3-hexadiene, 2,4-hexadiene, 1-methyl-1-cyclopentene, 3-methyl-1,3-pentadiene, 3-methyl-1,4-pentadiene and methylenecyclopentane.

8. The paraffin purification method according to claim 1, wherein the source material contains 98-99.5 mol % of propane and 0.5-2.0 mol % of propylene.

* * * * *